United States Patent [19]

Pitzele et al.

[11] 4,374,932
[45] Feb. 22, 1983

[54] 5-ASA DRUG DELIVERY SYSTEM

[75] Inventors: Barnett S. Pitzele, Skokie; Peter H. Jones, Lake Bluff, both of Ill.

[73] Assignee: G. D. Searle & Co., Skokie, Ill.

[21] Appl. No.: 271,748

[22] Filed: Jun. 8, 1981

[51] Int. Cl.$^3$ .................. B01J 41/14; A61K 31/74
[52] U.S. Cl. .................................. 521/32; 521/28; 424/79
[58] Field of Search ............................ 521/28; 424/79

[56] References Cited

U.S. PATENT DOCUMENTS 2,697,059 12/1954 Gustus ................................ 424/79
2,721,827 10/1955 Gustus ................................ 424/79
2,990,332 6/1961 Keating et al. ..................... 424/79
3,143,465 8/1964 Keating et al. ..................... 521/28

Primary Examiner—Joseph L. Schofer
Assistant Examiner—Peter F. Kulkosky
Attorney, Agent, or Firm—James G. Passe

[57] ABSTRACT

The present invention relates to novel compounds for the prophylaxis and treatment of Inflammatory Bowel disease (IBD) via the administration of an effective amount in a suitable pharmaceutical dosage of a polymeric agent for releasing 5,5'-azobis-salicylic acid which comprises a non-degradable anionic exchange resin and the dianionic form of 5,5'-azobis-salicylic acid. The 5,5'-azobis-salicylic acid undergoes bacterial cleavage in the mammalian lower bowel to release 5-aminosalicylic acid.

2 Claims, No Drawings

5-ASA DRUG DELIVERY SYSTEM

BACKGROUND OF THE INVENTION

The present invention provides novel compounds for the treatment of Inflammatory Bowel Disease (IBD). In particular it provides a compound according to formula I of Chart A, a pharmacologically acceptable polymeric agent for releasing 5,5'-azobis-salicylic acid (formula V of Chart A) which comprises a non-degradable anionic exchange resin (R) and the dianionic form of 5,5'-azobis-salicylic acid.

IBD is a chronic, nonspecific, inflammatory and ulcerative disease of the small intestine and/or colon, and may be characterized by bloody diarrhea. An example is ulcerative colitis. In ulcerative colitis the disease begins in the rectosigmoid area and may extend proximally, eventually involving the entire colon, or it may involve the large bowel all at once. See Cecil, Textbook of Medicine, 1568–1578.

Treatment of IBD has been accomplished by several Pharmaceutical compounds. Notably, adrenocorticosteroids, belladonna alkaloids, belladonna derivatives, bismuth subcarbonate, kaolin and sulfasalazine are in current use. The adrenocorticosteroids may mask symptoms of intestine perforation and peritonitis and are generally only used for short term therapy, (Goodman and Gilman 4th Ed. pg. 1634 (1970) and major complications may occur despite corticosteroid therapy. The belladonna alkaloids and derivatives are largely considered ineffective in IBD. (Goodman and Gilman 4th Ed. pg. 544 (1970). Bismuth subcarbonate is a mechanical protectant and merely prevents further irritation of the condition without any direct effect on the condition. Kaolin is an absorbent which absorbs bacteria and toxins in the colon, but it is doubtful that appreciable activity is retained by the time it reaches the lower bowel. (Goodman and Gilman 4th ed. pg. 990 (1970). Sulfasalazine (SS) is the drug of choice currently for IBD. Its structure is shown in formula II of Chart A. SS is a pro-drug, that is, upon administration, biological processes act upon SS to produce the drug which has the desired biological activity. Upon oral administration, about one-third of a given dose of SS is absorbed from the small intestine. The remaining two-thirds is split in the colon by azo-reductase from bacterial flora into sulphapyridine (SP), formula II of Chart A, and 5-aminosalicylic acid (5-ASA) formula IV of Chart A. (Physican's Desk Reference 31st ed. pg. 1250 (1977) See also Klotz, New Eng J. of Med 303, 1499 (1980). It has been determined that the activity of SS comes from the 5-ASA produced. SS is effective as a pro-drug because its *relative* insolubility prevents its complete absorption in the small intestine thus allowing delivery of SS to the site of action, i.e., the large intestine. Given separately, both SP and 5-ASA are almost completely absorbed from the small intestine. While effective, SS has several severe side effects including blood dyscrasias and hypersensitivity reactions. This toxicity of SS is due almost entirely to the SP produced.

PRIOR ART

The pharmacological treatment of IBD is well known as indicated above. SS is described in U.S. Pat. No. 2,396,145 (1946). 5,5'-azobis-salicylic acid is described in Great Britain Pat. No. 408,676 (1934). The only use described is as a dyestuff. A number of articles have described the therapeutic effectiveness of 5-ASA and SS, its efficacy, as well as the toxicity problems of SS. Of note is Khan, et al, *The Lancet*, 292, Oct 29, (1977); Hees, et al, *Gut* 21, 632–635 (1980) and Klotz, et al, *N. Engl. J Med* 303, 1499–1502 (1980). U.S. Pat. No. 4,190,716 discloses a polymer consisting of an organic polymer backbone containing aromatic rings which are covalently bonded via azo bonds to a plurality of salicylic acid or salicylate salt groups. The present invention, in contrast, provides an ionically bonded 5,5'-azobis-salicylic acid.

SUMMARY OF THE INVENTION

The present invention particularly provides a polymeric anionic exchange complex of formula I which comprises a pharmacologically acceptable non-degradable anionic exchange resin (R) which has a molecular size which precludes its absorption from the intestinal lumen and the dianionic form of 5,5'-azobis-salicylic acid.

By ionicaly bonding the 5,5'-azobis-salicylic acid to the polymers of the invention a drug delivery system is created which bypasses absorption in the stomach and small intestine. The polymer complex decreases the absorption of 5,5'-azobis-salicylic acid until it reaches the lower bowel. Release in this manner enables delivery of the 5,5'-azobis-salicylic acid to the site of action. The compounds of the instant invention are useful in that the 5,5'-azobis-salicylic acid thereby released is readily reduced to 5-ASA in the colon by intestinal bacteria. The polymeric portion of the complex is of a size that is excreted in the feces without absorption. 1 Mole of 5,5'-azobis-salicylic acid which is released from the polymer complex is bacterially cleaved to yield 2 moles of active 5-ASA. This means that a lower molar concentration of compound can be used than with previous compounds and release systems (e.g. sulfasalazine). In addition the reduction is accomplished without a potentially toxic compound being produced.

In general, any anionic exchange resin sufficiently basic to deprotonate a derivatized benzoic acid can be used to make the compounds of this invention. A prefered anionic exchange resin is AG1-X2. The anionic exchange resin AG1-X2 is purchased from Bio-Rad as 200–400 mesh beads in the chloride form. It is converted to hydroxide form using aqueous NaOH and rinsed with distilled water.

AG1-X2 is initially manufactured by Dow (as Dowex 1-X2) and purified by Bio-Rad. It is a polystyrene polymer cross-linked with 2 percent divinylbenzene (N.B: the origin of the "X2" part of the name), and it is functionalized on the benzene ring with a methylene trialkylammonium residue (giving the resin a permanent positive charge). Such a resin is a "strongly ionic" exchanger.

By virtue of the anti-IBD activity, 5,5'-azobis-salicylic polymeric exchange complexes are useful in treating IBD in humans and animals. A physician of ordinary skill could readily determine a subject who is exhibiting IBD symptoms. Regardless of the route of administration selected, the compounds of the present invention are formulated into pharmaceutically acceptable dosage forms by conventional methods known to the pharmaceutical art.

The compounds can be administered in such oral unit dosage forms as tablets, capsules, pills, powders, suspension or solution or granules. They also may be administered rectally in such forms as suppositories, creams, ointments, enemas and the like. An effective but nontoxic quantity is employed in treatment. The dosage regimen for prevention or treatment of IBD by the compounds of this invention is selected in accordance with a variety of factors including the type, age, weight, sex and medical condition of the mammal, the severity of the IBD and the route of administration. An ordinarily skilled physician or veterinarian could employ relatively low dosage at first, subsequently increasing the dose until a maximum response is obtained.

Initial dosages of the compounds are ordinarily in the area of 5 mg/kg up to at least 100 mg/kg orally.

DESCRIPTION OF THE PREFERRED EMBODIMENTS

The compounds of the present invention are useful in the treatment of IBD as shown by the following test.

EXAMPLE 1

In Vitro Bacterial Incubation

No animal model exists for testing the efficacy of therapeutic modalities for the treatment of IBD. The following test determines the reduction of azo bonds of 5,5′-azobis-salicylic acid by colonic bacteria in order to release 5-ASA.

1. Sample Preparation: Two pure bacterial cultures normally found in the colon were used: *Klebsiella pneumoniae* (ATCC4352) in trypticase soy broth; and *Bacteroides fragilis* (ATCC23745) in fluid thioglycollate medium. Compounds dissolved or suspended in DMSO were added to 5 ml of sterile media or to 5 ml of media which had been inoculated with bacteria 24 hours previously. Each time a compound was incubated, additional inoculates were incubated with 5-ASA and SS. Each 100 ml of DMSO contained the same molar equivalents of 5-ASA. Cultures and control media were incubated for 45–48 hours at 37° C.

2. Sample Analysis: Bacterial cultures and control media were filtered with a final filter size of 0.45 microns. The filtrates were applied directly to Merck GF-254 silica TLC plates (EM Laboratories, Darmstadt, Germany) along with 5-ASA standards at various concentrations from 50 ng to 450 ng/5 µl. Additionally, standards of SS and each compound were also applied to the TLC plate. Plates were developed to 16 cm in saturated tanks of three types:

(a) Ethanol:NH$_4$OH (99:1, v/v)
(b) Butanol:Butanone:H$_2$O (40:40:20, v/v)
(c) Isopropanol:H$_2$O:NH$_4$OH (70:20:10, v/v)

Plates were examined within 10 minutes after development under longwave U.V. (365 nm) light and the intensity of the green fluorescence produced by 5-ASA (produced by azo-reduction of compounds of the invention) was compared to 5-ASA standards, 5-ASA incubated with bacteria, and SS incubated with bacteria.

In this test the amount of 5-ASA produced after incubation in contact with bacteria is a measure of the degree of azo-reduction of invention compound to 5-ASA by bacteria. Comparison of these compounds with the data derived from SS would reveal those compounds that release equivalent amounts of 5-ASA under identical conditions. Controls acted as a check to show that without bacteria, no azo-reduction took place, and that the compound or any breakdown products did not fluoresce green at the same R$_f$ as 5-ASA. Therefore, these data provided evidence that the reductive release of 5-ASA from 5,5′-azobis-salicylic acid occurs.

TABLE 1

| Compound | Percent Formation of 5-ASA[1] | |
|---|---|---|
|  | Bacteroides Culture | Klebsiella Culture |
| Sulfasalazine (SS) | 100 | 100 |
| 5,5′-azobis-salicylic acid | 100 | 75 |
| (AG1-X2)$_2$ 5,5′-azobis-salicylic acid complex | 100 | 75 |

[1]Formulation of 5-ASA is compared to that released by SS, which is defined as 100 percent.

EXAMPLE 2

(AG 1-X2)$_2$ 5,5′-azobis-salicylic acid complex (Formula 1:R is AG1-X2).

BioRad AG 1-X2 (chloride form), 200–400 mesh (0.8 meq/ml) is suspended in water and loaded onto a 2.5 cm diameter glass column. A total of 220 ml wet resin is used. The column is flushed with distilled water. NaOH in H$_2$O, 10 percent wt/vol., is then slowly passed through (ca L ml/min). A total of 500 ml NaOH solution is passed through. The column is then washed with distilled water. The wash is continued until the pH of the eluate (indicating paper) is under 7. 47.5 ml of this resin is combined with 5.7 g of 5,5′-azobis-salicylic acid in 250 ml distilled water. This mixture is refluxed for 16 hr then filtered while warm, and the resin is washed with distilled water. The resin is dried in a vacuum (aspirator) oven at 60° for 16 hr to yield the title compound. The title compound is approximately 40 percent 5,5′-azobis-salicylic acid by weight.

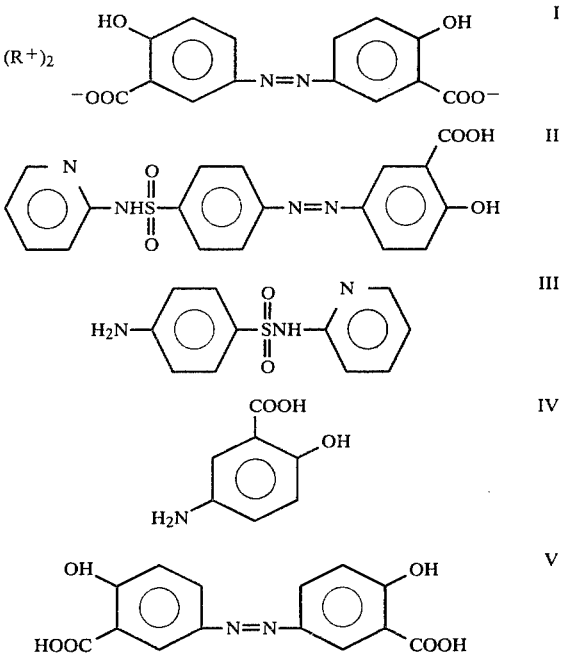

CHART A

What is claimed is:

1. A polymeric anionic exchange complex comprising a pharmacologically acceptable, non-absorbable, non-degradable anionic exchange resin and the dianionic form of 5,5′-azobis salicylic acid.

2. A complex according to claim 1 wherein the resin is a polystyrene polymer cross-linked with 2% divinylbenzene and functionalized on the benzene ring with a trialkyl ammonium methyl group.

* * * * *